United States Patent
Hansell

(10) Patent No.: US 12,035,945 B2
(45) Date of Patent: *Jul. 16, 2024

(54) CONFORMING BONE STABILIZATION RECEIVER

(71) Applicant: GLOBUS MEDICAL, INC., Audubon, PA (US)

(72) Inventor: Noah Hansell, King of Prussia, PA (US)

(73) Assignee: Globus Medical, Inc., Audubon, PA (US)

( * ) Notice: Subject to any disclaimer, the term of this patent is extended or adjusted under 35 U.S.C. 154(b) by 632 days.

This patent is subject to a terminal disclaimer.

(21) Appl. No.: 16/876,515

(22) Filed: May 18, 2020

(65) Prior Publication Data

US 2020/0275954 A1 Sep. 3, 2020

Related U.S. Application Data

(63) Continuation of application No. 16/173,303, filed on Oct. 29, 2018, now Pat. No. 10,682,163, which is a continuation of application No. 15/665,567, filed on Aug. 1, 2017, now Pat. No. 10,143,496, which is a continuation of application No. 14/799,607, filed on Jul. 15, 2015, now Pat. No. 9,750,541, which is a continuation of application No. 13/152,850, filed on Jun. 3, 2011, now Pat. No. 9,113,960.

(Continued)

(51) Int. Cl.
*A61B 17/88* (2006.01)
*A61B 17/70* (2006.01)

(52) U.S. Cl.
CPC ...... *A61B 17/7032* (2013.01); *A61B 17/7035* (2013.01); *A61B 17/7041* (2013.01)

(58) Field of Classification Search
CPC ............ A61B 17/7032; A61B 17/7035; A61B 17/7041
USPC ....... 606/266, 267, 268, 269, 270, 272, 278, 606/279, 305, 308, 328
See application file for complete search history.

(56) References Cited

U.S. PATENT DOCUMENTS 6,302,888 B1 * 10/2001 Mellinger .......... A61B 17/7032
411/405
8,636,776 B2 * 1/2014 Rosenberg ......... A61B 17/7086
606/270

(Continued)

FOREIGN PATENT DOCUMENTS

JP 6-296621 A 10/1994
JP 2008-534075 A 8/2008
(Continued)

*Primary Examiner* — Eduardo C Robert
*Assistant Examiner* — David C Comstock

(57) ABSTRACT

A receiver for engaging a bone stabilizing element includes a receiver portion connectable to the stabilizing element, and a base portion connectable to a bone of a patient. The base portion may connect to the bone with a bone screw, for example a polyaxial bone screw, and the receiver portion may connect to the stabilizing element, for example a rod, using a set screw. The receiver portion and the base portion are slideably connected to each other, coupled and constrained in relative movement, by overlapping portions. Axial rotation between the receiver portion and the base portion is enabled by changing the relative dimensions of overlapped portions.

19 Claims, 7 Drawing Sheets

Related U.S. Application Data

(60) Provisional application No. 61/352,680, filed on Jun. 8, 2010.

(56) References Cited

U.S. PATENT DOCUMENTS

| | | | |
|---|---|---|---|
| 2003/0045879 A1* | 3/2003 | Minfelde | A61B 17/7035 |
| | | | 606/279 |
| 2006/0235392 A1 | 10/2006 | Hammer | |
| 2007/0244482 A1* | 10/2007 | Aferzon | A61B 17/7038 |
| | | | 623/17.11 |
| 2009/0163955 A1* | 6/2009 | Moumene | A61B 17/701 |
| | | | 606/257 |
| 2009/0318973 A1* | 12/2009 | Moulin | A61B 17/701 |
| | | | 606/301 |
| 2010/0030272 A1* | 2/2010 | Winslow | A61B 17/7046 |
| | | | 606/264 |
| 2010/0030273 A1* | 2/2010 | Mitchell | A61B 17/7041 |
| | | | 606/264 |
| 2010/0241170 A1 | 9/2010 | Cammisa | |
| 2010/0262190 A1* | 10/2010 | Ballard | A61B 17/7005 |
| | | | 606/279 |
| 2010/0292739 A1* | 11/2010 | Schwab | A61B 17/7032 |
| | | | 606/301 |
| 2011/0112578 A1* | 5/2011 | Keiser | A61B 17/7032 |
| | | | 606/264 |
| 2011/0202094 A1* | 8/2011 | Pereira | A61B 17/7037 |
| | | | 606/305 |
| 2014/0200618 A1* | 7/2014 | Donner | A61F 2/4611 |
| | | | 606/281 |

FOREIGN PATENT DOCUMENTS

| | | |
|---|---|---|
| JP | 2010-505541 A | 2/2010 |
| JP | 2013-509952 A | 3/2013 |
| WO | 2011056707 A2 | 5/2011 |

* cited by examiner

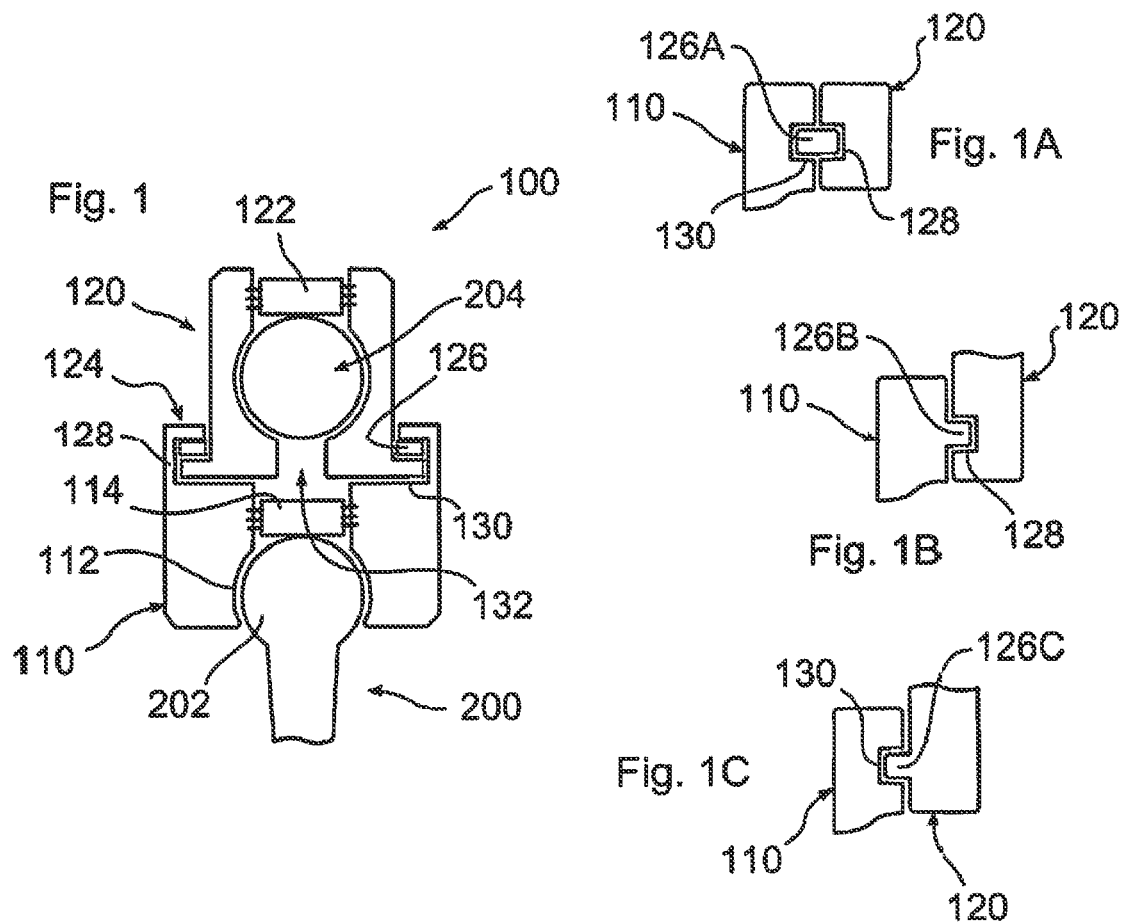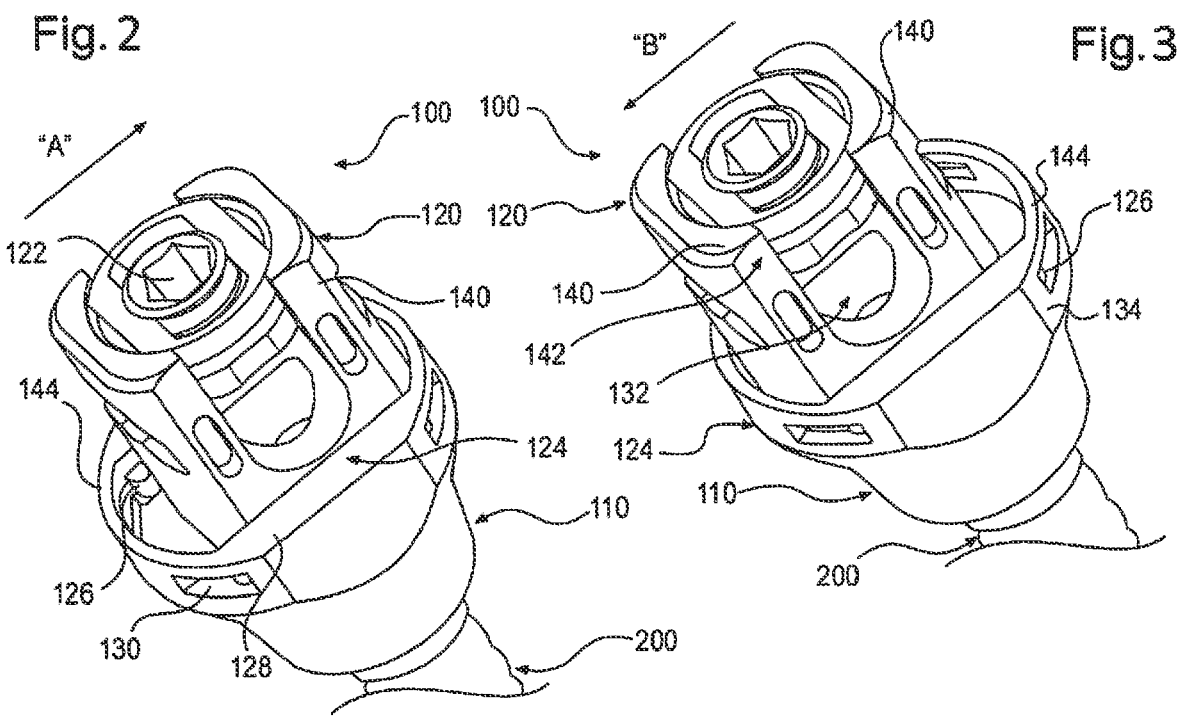

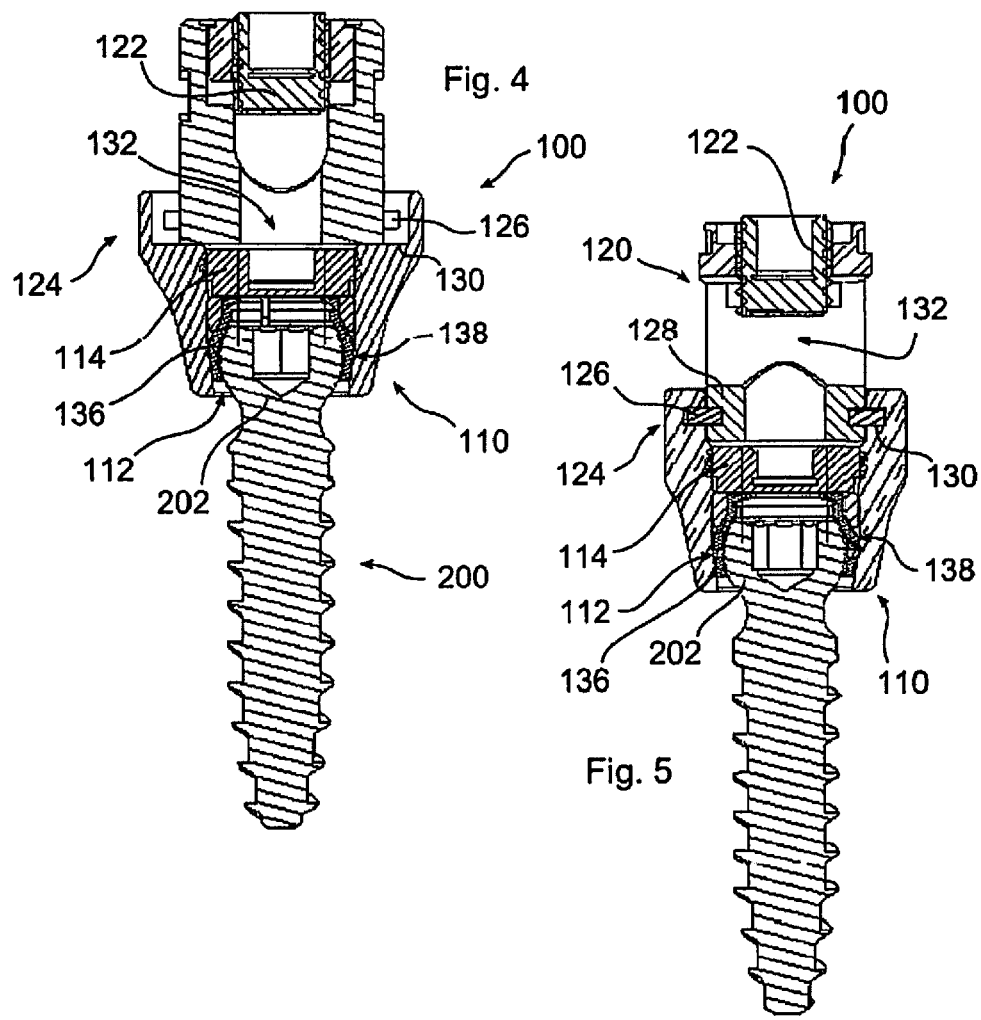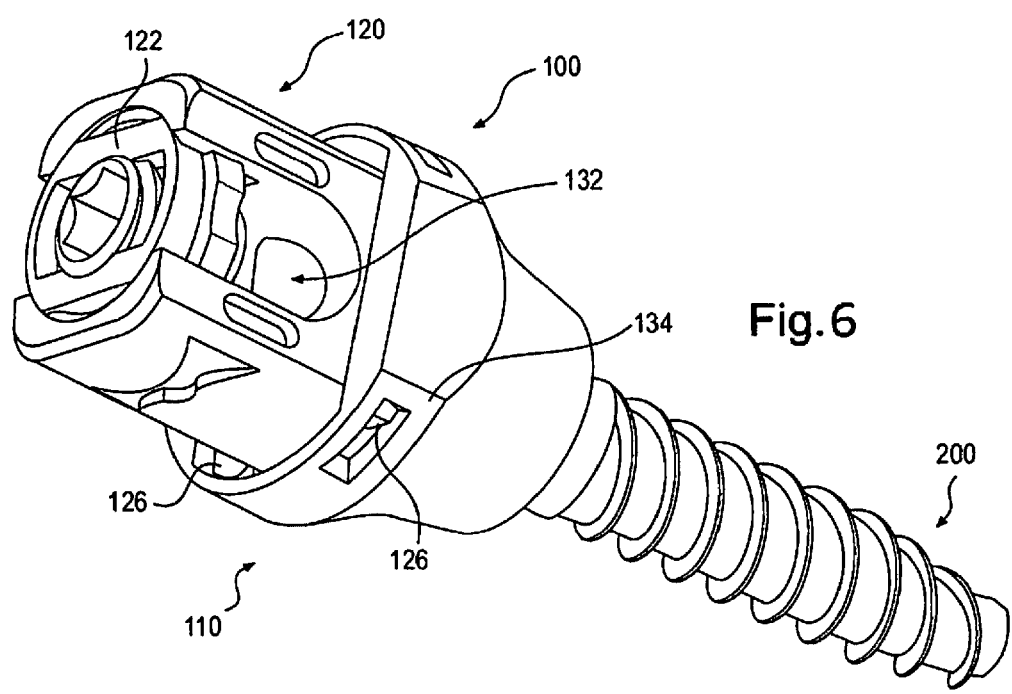

CONFORMING BONE STABILIZATION RECEIVER

CROSS-REFERENCE TO RELATED APPLICATIONS

This application is a continuation application of U.S. patent application Ser. No. 16/173,303 filed Oct. 29, 2018 (published as U.S. Pat. Pub. No. 2019/0059952), which is a continuation application of U.S. patent application Ser. No. 15/665,567 filed Aug. 1, 2017 (now issued as U.S. Pat. No. 10,143,496), which is a continuation application of U.S. patent application Ser. No. 14/799,607, filed Jul. 15, 2015 (now issued as U.S. Pat. No. 9,750,541), which is a continuation of U.S. patent application Ser. No. 13/152,850, filed Jun. 3, 2011 (now issued as U.S. Pat. No. 9,113,960), which claims priority to U.S. Provisional Application 61/352,680 , all of which are hereby incorporated by reference in their entirety.

FIELD OF THE INVENTION

The present invention relates to the stabilization of the spine, and particularly the stabilization of multiple vertebral levels, preserving natural motion within therapeutic boundaries.

BACKGROUND OF THE INVENTION

The vertebrate spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints and allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The vertebrae also contains four articular processes that extend from the posterior region of the vertebra. There are two articular processes on the left side of the vertebra and two articular processes on the right side of the vertebra. Two of the four processes (one on the left and one on the right) extend upwards from the top of the laminae and are referred to as the superior articular processes. The other two processes (again one on the left and one on the right) extend downwards from the bottom of the laminae and are referred as the inferior articular processes. In a healthy spine the left and right superior articular processes of a vertebra form synovial joints with the left and right inferior articular processes of the superior adjacent vertebra. These joints are also referred to as facet joints. The facet joints are synovial joints as the joints are encapsulated with connective tissue and lubricated by synovial fluid. The joint faces are also covered with smooth cartilage, which acts to reduce friction and absorb shock.

The intervertebral disc primarily serves as a mechanical cushion permitting controlled motion between vertebral segments of the axial skeleton. The normal disc is a unique, mixed structure, comprised of three component tissues: the nucleus pulpous (nucleus), the annulus fibrosus (annulus) and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The annulus of the disc is a tough, outer fibrous ring which binds together adjacent vertebrae. The fibrous portion, which is much like a laminated automobile tire, measures about 10 to 15 millimeters in height and about 15 to 20 millimeters in thickness. The fibers of the annulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the annulus is the nucleus. The healthy nucleus is largely a gel-like substance having high water content, and like air in a tire, serves to keep the annulus tight yet flexible. The nucleus-gel moves slightly within the annulus when force is exerted on the adjacent vertebrae while bending, lifting, and other motions.

The spinal disc may be displaced or damaged due to trauma, disease, degenerative defects, or wear over an extended period. A disc herniation occurs when the annulus fibers are weakened or torn and the inner tissue of the nucleus becomes permanently bulged, distended, or extruded out of its normal, internal annulus confines. The mass of a herniated or slipped nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all discal motion is lost in the fused segment. Ultimately, this procedure places a greater stress on the discs adjacent to the fused segment as they compensate for lack of motion, perhaps leading to premature degeneration of those adjacent discs.

As an alternative to vertebral fusion, various prosthetic discs have been developed. The first prosthetics embodied a wide variety of ideas, such as ball bearings, springs, metal spikes and other perceived aids. These prosthetics are all made to replace the entire intervertebral disc space and are large and rigid. Many of the current designs for prosthetic discs are large and inflexible. In addition, prosthetic disc sizes and other parameters limit the approach a surgeon may take to implant the devices.

For example, many of these devices require an anterior implantation approach as the barriers presented by the lamina and, more importantly, the spinal cord and nerve rootlets during posterior or posterior lateral implantation is difficult to avoid. Anterior implantation involves numerous risks during surgery. Various organs present physical obstacles as the surgeon attempts to access the damaged disc area from the front of the patient. After an incision into the patient's abdomen, the surgeon must navigate around organs and carefully move them aside in order to gain access to the spine. Additionally, the greater vessels are presented during an anterior approach. These greater vessels (the aorta and vena cava) risk exposure and injury during surgery. One risk to the patient from an anterior approach is that their organs may be inadvertently damaged during the procedure. Another risk to the patient from an anterior approach is that their greater vessels may be injured during surgery. These constraints and/or considerations have led to novel prosthetic disc designs as disclosed in co-pending U.S. patent application Ser. No. 11/246,149, which is incorporated herein by reference in its entirety.

A posterior approach to intervertebral disc implantation avoids the risks of damaging body organs and vessels. Despite this advantage, a posterior approach raises other difficulties that have discouraged it use. For instance, a posterior approach can introduce a risk of damaging the spinal cord. For example, vertebral body geometry allows only limited access to the intervertebral discs and a posterior approach usually requires the retraction of the spinal cord to one side, or the other, or both during surgery. Because of the spinal chord's importance in the human body, reducing exposure of the spinal cord to injury during surgery is important. Thus, the key to successful posterior or posterior lateral implantation is avoiding contact with the spinal cord, as well as being able to place an implant through a limited area due to the shape of the vertebral bones. These constraints and/or considerations have led to novel prosthetic disc designs as disclosed in co-pending U.S. patent application Ser. No. 10/909,210, which is incorporated herein by reference in its entirety.

Another known approach to the intervertebral space is the transforminal approach. This approach has been used in interbody lumbar fusion surgeries and involves approaching the intervertebral space through the intervertebral foramina. This approach often requires the removal of one facet joint on either the left or right side. After removal, the surgeon gains access to the intervertebral space through the intervertebral foramina. One drawback to this method is that the removal of a facet joint may lead to instability of the spine. Despite this drawback, in many instances the transforminal approach is favored in that there is reduced risk to the organs and greater vessels (as compared to the anterior approach) and reduced risk to the spinal cord (as to the posterior approach). A stabilization structure may be utilized on the posterior region of the spine to reduce the potential instability created by the facet removal.

SUMMARY OF THE INVENTION

In accordance with the invention, a device is provided for connecting a stabilizing member to one or more bones of a patient, comprising a base having a first and second axis, the base including means for connecting the base to the bone; a receiver having a first and second axis, the receiver positionable upon the base and including means for connecting the receiver to the stabilizing member; a slide rail associated with one of the base or the receiver; and a projection connected to the other of the base or receiver associated with the slide rail, insertable in apposition to the slide rail, operative when inserted to limit respective movement of the base and the receiver in a direction aligned with their respective first axes, and to slideably limit relative movement of the base and the receiver in a direction aligned with their respective second axes.

Various embodiments of the invention further include: a second projection connectable to one of the base and the receiver, operable to limit a lateral movement of the receiver relative to the base; means for connecting the base to the bone includes a chamber for a bone screw, and means for clamping the head of the bone screw within the chamber; means for connecting the receiver to the stabilizing member includes a yoke and a set screw; the projection is polymeric; the slide rail is a flange extending along at least two sides of the base or receiver to which it is associated; the slide rail is a face of a channel formed in the base or receiver to which it is associated; the projection is a flange extending along at least two sides of the base or receiver which is not associated with the slide rail; the projection lies between the slide rail and a portion of the base or receiver which is not associated with the slide rail; the first axes of the receiver and the base extend in a direction corresponding to a sagittal plane of the body, when the base is connected to the body, and the receiver is positioned upon the base; the receiver slides upon the base in a direction corresponding to their mutual second axes; a gap between the inserted projection and the slide rail, enables a therapeutically beneficial amount of relative movement between the receiver and the base, in a direction corresponding to the first axes; at least two receivers are connected to bones of the patient, the stabilizing member extending between adjacent receivers; a portion of the stabilizing member is connected to the device, and another portion of the stabilizing member is connected to the patient by another means; the one or more bones of a patient are selected from the group consisting of: toe, foot, ankle, calf, knee, thigh, hip, spine, shoulder, head, jaw, upper arm, elbow, lower arm, wrist, hand, finger; the stabilizing member is either rigid or flexible.

Alternatively, a device of the invention is provided for connecting a stabilizing member to one or more bones of a patient, comprising: a base having a first and second axis, the base including a base threaded fastener for connecting the base to the bone; a receiver having a first and second axis, the receiver slidingly positionable upon the base and including a receiver threaded fastener for connecting the receiver to the stabilizing member; a slide rail associated with one of the base or the receiver; a projection connected to the other of the base or receiver to which the slide rail is associated, insertable in apposition to the slide rail, operative when inserted to limit respective movement of the base and the receiver in a direction aligned with their respective first axes, and to slideably limit relative movement of the base and the receiver in a direction aligned with their respective second axes; and an access channel extending in a direction of the first axes of each of the base and the receiver, in communication with the base threaded fastener.

Other embodiments include: the receiver threaded fastener is disposed within the channel; and the receiver and base threaded fasteners are positioned within the access channel when the device is connected to the patient.

In another alternative, a device of the invention provides for connecting a stabilizing member to one or more bones of a patient, comprising: a base having a first and second axis, the base including a base threaded fastener for connecting the base to the bone; a receiver having a first and second axis, the receiver slidingly positionable upon the base and including a receiver threaded fastener for connecting the receiver to the stabilizing member; an elongated aperture connected to one of the base or the receiver; a projection connected to the other of the base or receiver to which the elongated aperture is connected, the projection projecting within the elongated aperture, operative thereby to therapeutically limit respective movement of the base and the receiver in a direction aligned with their respective first axes, and to slideably and therapeutically limit relative movement of the base and the receiver in a direction aligned with their respective second axes to a greater extent than the movement aligned with their respective first axes; and an access channel extending in a direction of the first axes of each of the base and the receiver, in communication with the base threaded fastener

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 1 is a schematic cross section of a stabilizing receiver in accordance with the invention;

FIGS. 1A-1C depict alternative engagement embodiments of the receiver of FIG. 1;

FIG. 2 is a perspective view of a stabilizing receiver in accordance with the invention, shifted in a first direction;

FIG. 3 illustrates the receiver in accordance with FIG. 2, shifted in a second direction;

FIG. 4 is a cross sectional illustration of the receiver of FIG. 2, taken along a longitudinal centerline of the receiver;

FIG. 5 is a cross sectional illustration of the receiver of FIG. 2, taken along a longitudinal centerline of the receiver, rotated 90 degrees with respect to FIG. 4;

FIG. 6 is an alternative perspective view of the receiver of FIG. 2, together with a bone screw to which it is connected;

DETAILED DESCRIPTION OF THE INVENTION

Figures 7, 8, 9:
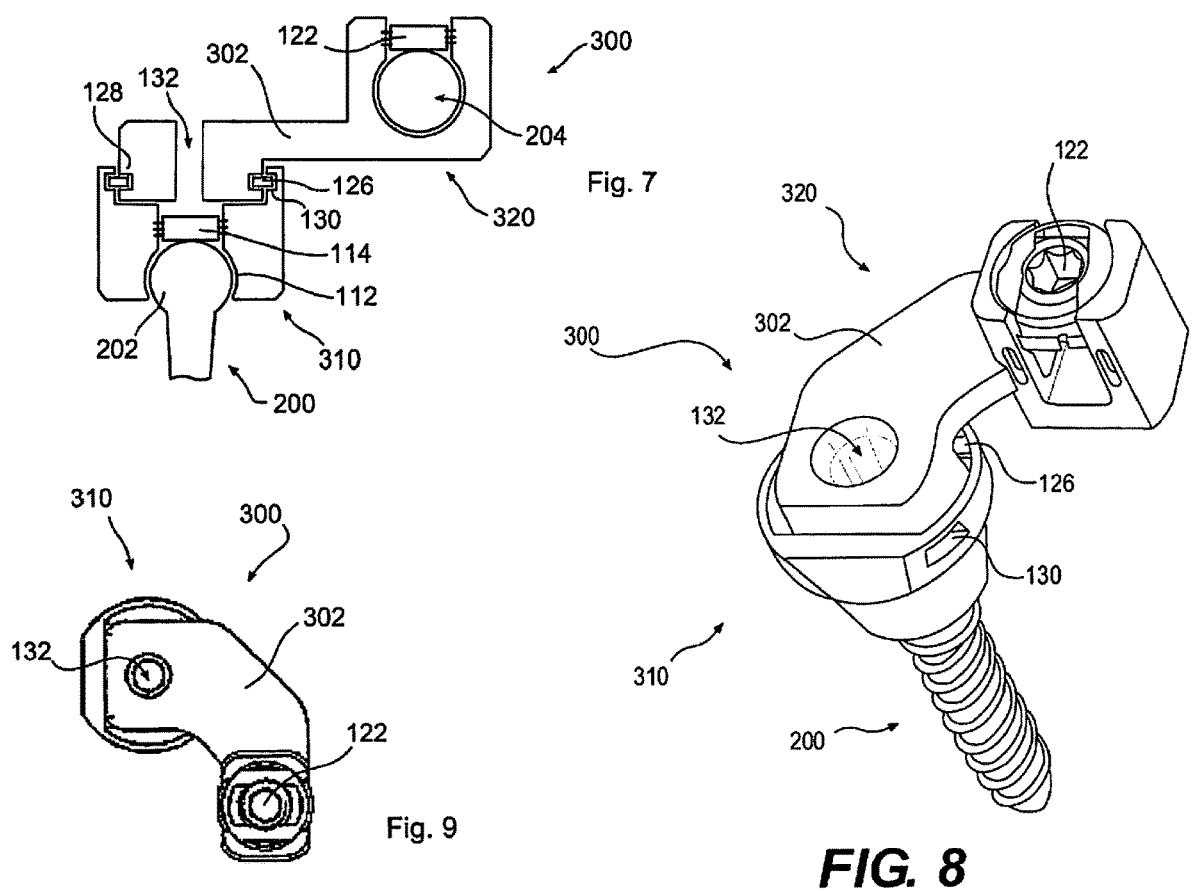
FIG. 7 is a schematic cross section of a stabilizing receiver of the invention, provided with a lateral offset.
FIG. 8 is a perspective view of a stabilizing receiver having a lateral offset, in accordance with the invention.
FIG. 9 is a schematic view of the receiver of FIG. 8.

During certain surgical procedures on bones, including but not limited to the spine, it may become necessary to supplement or even entirely replace the functionality of one or more joints. Attendant with these procedures is a desire to mimic, as best as possible, a natural movement of a healthy joint. Various devices and methods are known for fixing adjacent vertebrae, one to the other, while enabling movement within constraints, such as are disclosed in U.S. Patent Application Publication Nos. 2009/0299411 to Laskowitz et al., 2009/0240285 to Friedrich et al., or 2009/0240286 to Friedrich et al., the contents of each of which are incorporated by reference herein in their entirety. The present invention provides a device and method which may be used alone, or in combination with such devices and methods, for providing an additional or alternative range of motion, within constraints, thereby improving a therapeutic benefit to the patient, and providing additional options for the medical practitioner.

With reference to FIG. 1, a stabilizing receiver 100 of the invention is formed with an anchor base 110 operative to securely connect receiver 100 to an anchor 102. Anchor base may connect to anchor by any known means, including a threadable attachment, set screw, welding, or may be integrally formed with anchor 200. Anchor 200 includes any means for attaching anchor base 110 to the body, including adhesives, projections, screws, pins, or other method. In accordance with one embodiment of the invention, anchor 102 is advantageously a polyaxial bone screw, as depicted, and anchor base 110 includes a bone screw chamber 112 for conformingly and movably receiving a polyaxial bone screw head 202. Anchor fastener 114 is provided, operative to secure bone screw head 202 within anchor base 110, to thereby lock anchor 200 in a fixed position with respect to anchor base 110. In the embodiment of FIG. 1, anchor fastener 114 depicts a set screw, although other means may be provided to apply pressure or firmly secure an anchor, including collars, sleeves, and the like, as more fully disclosed, for example, in U.S. patent application Ser. Nos. 10/819,994 and 11/146,147, which are incorporated by reference herein.

FIG. 1 further depicts a receiver assembly 120 operative to securely retain a stabilizing means 204, which may include a rod, depicted, or a pin, brace, spring, cord, resilient extension, or any other stabilizing device, such as are disclosed, for example, in the patents and applications previously incorporated, or as further described in U.S.

patent application Ser. Nos. 10/443,755 and 10/762,533, which are incorporated by reference herein. Receiver assembly 120 advantageously includes a stabilizer fastener 122, in this embodiment a set screw, operative to secure stabilizing means 204 in a fixed position within receiver assembly 120.

In the embodiment of FIG. 1, receiver assembly 120 and anchor base 110 are mutually connected by a flanged connection 124, formed by a tenon, sash, projection, or tiebar 126, slideably retained within slide rails, flanges, or channels, including a receiver channel 128, and an anchor channel 130. Tiebar 126 and or channels 128, 130 are advantageously formed with a lubricious material, favoring smooth movement of channels 128, 130 in contact with tiebar 126. Example materials include ultra high molecular weight polyethylene (UHMWPE), PEEK, or other biocompatible polymer, or ceramic, polished metal, or other suitable biocompatible material. In one embodiment, tiebar 126 is a polymer, and channels 128, 130 are metal.

An access bore 132 extends from anchor fastener 114, through receiver assembly 120, whereby before stabilizing means 204 and stabilizer fastener 122 are installed, anchor 200 may be installed, or anchor fastener 114 may be installed, after which the aforementioned elements may be adjusted or tightened.

FIGS. 1A, 1B, and 1C illustrate alternative configurations for flanged connection 124. In FIG. 1A, each of receiver assembly 120 and anchor base 110 form a channel on three sides of tiebar 126A, in the manner of a dovetail. It should be understood that the mating engagement of tiebar 126 and channels 128, 130 may incorporate any of the more complex shapes known in the art of forming dovetails, including fan shaped mating components, which avoid a separation of the mated components.

In FIG. 1B, tiebar 126B is formed integrally, as a projection, with anchor base 110, and in FIG. 1C, tiebar 126C is formed integrally with receiver assembly 120. In these embodiments, it may be advantageous to form a lubricious coating on one or more of the mating parts 126A/B and its corresponding channel. The embodiment of FIG. 1 or 1A enables the replacement of tiebar 126 without a requirement to remove other implanted components of device 100.

Referring now to FIGS. 2 and 3, an embodiment of a stabilizing receiver 100 is illustrated in perspective. FIG. 2 illustrates receiver assembly 120 shifted, in this perspective, to the right with respect to anchor base 110, and FIG. 3 illustrates receiver assembly 120 shifted to the left. In this embodiment, tiebar 126 is held stationery within anchor base 110 by a flange 134, indicated in FIG. 3. During its installation, tiebar 126 may be bent to pass over flange 134, whereupon after entering the channel, it may resiliently straighten and become trapped within the space between channels 128, 130, and flange 134 on each end. Other means of retaining tiebar 126 would be understood by those skilled in the art, including the use of pins, mating engagements, or a pressure fit.

Once tiebar 126 is inserted, receiver assembly 120 may slide laterally in connection with anchor base 110, channel 128 and or 130 sliding along a surface of tiebar 126. Receiver assembly 120 may not separate from anchor body 110, however, as tiebar 126 now occupies a clearance between receiver assembly 120 and anchor body 110 which enable their mutual assembly. Specifically, a projection of one of receiver assembly 120 or anchor base 110 was able to be inserted beneath a rail of the other, first on one side, then on another, until receiver assembly 120 was seatable upon anchor base 110. A limiting projection 144 on one of receiver assembly 120 or anchor base 110 servers to limit lateral movement of the respective parts. In FIG. 2, limiting projection 144 is integrally formed as an edge or rail of anchor base 110. In FIG. 13A, it is visible as a boundary edge of channel 428. Limiting projection may also be installable onto either receiver assembly 120 or anchor base 110, for example it may have the form of a pin or a screw which blocks the relative movement of the respective parts at an intended limit of travel.

Figure 13:
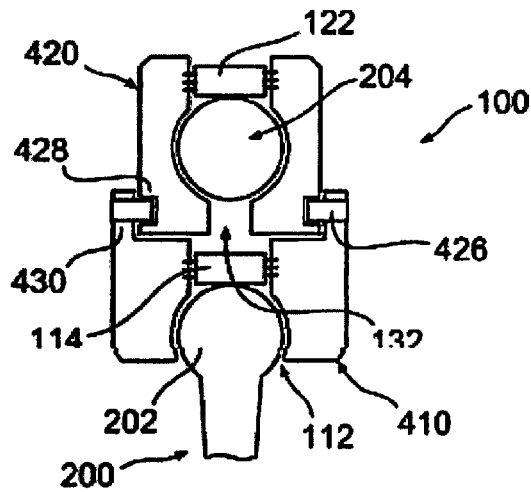
FIG. 13 is a schematic cross section of a stabilizing receiver in accordance with the invention, enabling conforming shifting in two dimensions.
Figure 13A:
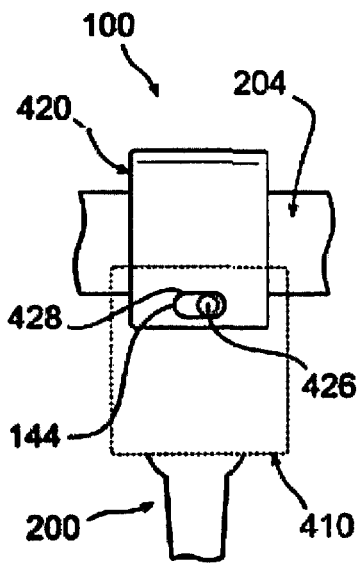
FIG. 13A is a schematic cross section of an upper portion of the stabilizing receiver of FIG. 13, rotated 90 degrees with respect to FIG. 13.

In the embodiment illustrated in FIGS. 2 and 13, stabilizing fastener 112 engages an aperture formed by two yoke extensions 140, through an interlocking channel 142 in either stabilizing fastener 112 or yoke extensions 140, and a corresponding flange 144 in the other of the two elements. In one embodiment, stabilizing fastener is turned about 90 degrees to engage interlocking channel 142 and flange 144, after which set screw 122 may be turned to secure a stabilizing means 204 which has been placed between yoke extensions 140. Examples of this may be found in U.S. patent application Ser. Nos. 10/819,994 and 11/146,147, which are incorporated by reference herein. Other means may be provided to apply pressure or firmly secure stabilizing means, including for example collars, sleeves, screws and the like, as are more fully disclosed, for example, in the incorporated patents and applications.

FIGS. 4 and 5 each depict a cross section of the receiver of FIGS. 2 and 6, taken through a longitudinal centerline thereof, in which bone screw chamber 112 is visible. FIG. 5 illustrates the cross section of FIG. 4, rotated 90 degrees along a longitudinal axis. One or more wedges 136 are advantageously driven into a space between an inner wall 138 of bone screw chamber 112, and bone screw head 202, causing wedges 136 to bear against both elements, thereby improving a strength of connection of bone screw 200 within receiver 100.

With reference to FIGS. 7-9, an alternative embodiment of the invention in the form of an offset receiver 300, provided with an offset extension 302 operative to displace offset receiving assembly 320 away from an axial centerline of anchor base 310. Elements of anchor base 310 are as described for anchor base 110, although as may be seen in FIGS. 7-9, access bore 132 is not obstructed after the installation of stabilizer fastener 122, or stabilizing means 204.

Figure 12:
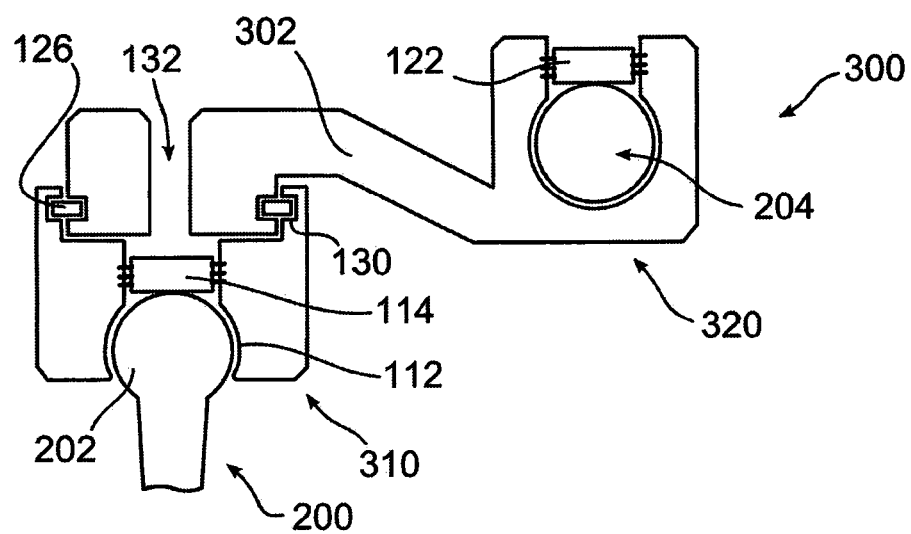
FIG. 12 is a schematic cross section of a stabilizing receiver in accordance with the invention, provided with an receiver assembly offset in three dimensions.

FIG. 8 illustrates offset receiver 300 in perspective, where it can be seen that offset extension 302 enables a location of offset receiving assembly 320 to a location removed from a location of anchor base 310. Moreover, offset extension 302 may advantageously have a complex geometry, and in particular can extend in a first direction, then turn, and then extend in a second direction. In this manner, offset extension 302 can reach around other objects, for example stabilizing elements, or a physiological structure, such as a bone pedicle. Further, offset extension 302 can provide an offset in three dimensions, as may be seen in FIG. 12.

Figure 10:
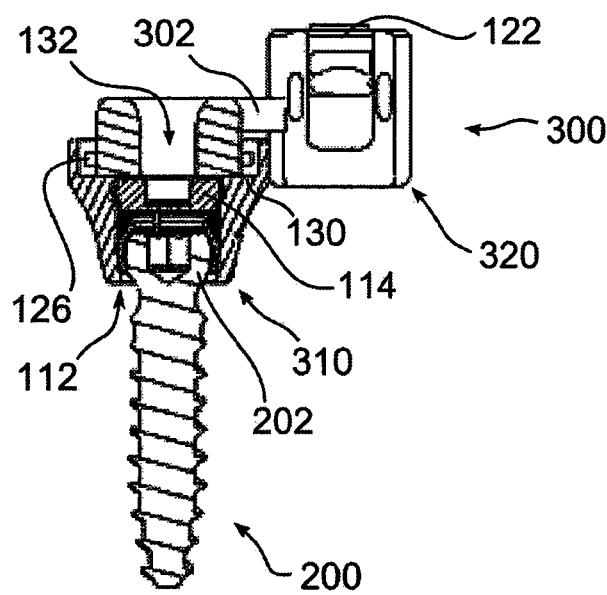
FIG. 10 is a cross sectional illustration of the receiver of FIG. 8, taken along a longitudinal centerline of the receiver.
Figure 11:
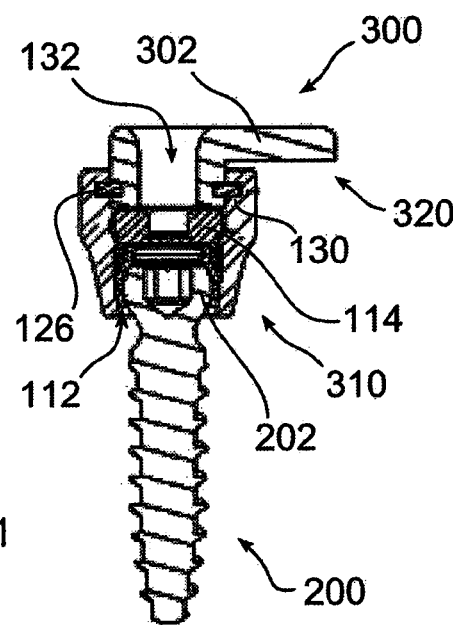
FIG. 11 is a cross sectional illustration of a receiver of the invention having an offset portion, taken along a longitudinal centerline of the receiver.

FIGS. 10 and 11 each depict a cross section of the receiver of FIG. 8, taken through a longitudinal centerline thereof. FIG. 11 illustrates the cross section of FIG. 10, rotated 90 degrees along a longitudinal axis, and with offset receiving assembly 320 not illustrated, for clarity.

In FIGS. 13-16, another embodiment of the invention is illustrated, in which defined therapeutically effective amounts of both lateral shifting and axial rotation are enabled. In FIG. 13, pin 426 is illustrated, operative to replace tiebar 126, and to provide additional range of motion. In the embodiment shown, pin 426 is securely retained within channel 430, for example by being press fit, adhered, or threadably engaged, and extends into channel 428 to be movable received therein; however, it should be understood that pin 426 could be securely retained within channel 428, and movably extend into channel 430. Channel 428 has the shape of an elongated opening, bore, or channel, whereby receiver assembly 420 is retained in connection with anchor base 410, but is free to rotate around its longitudinal axis to an extent defined by the length of channel 428, and the relative dimensions of pin 426. Similarly, receiver assembly 420 is free to shift sideways with respect to anchor base 410, with an extent of shifting being dependent upon the length of channel 428, and the relative dimensions of pin 426. A therapeutically effective amount of shifting or rotation is more than that which would be allowed by mere incidental spacing or a manufacturing tolerance needed for smooth relative movement of mating parts, but not more than would be deleterious to the patient.

Advantageously, pin 426 is sufficiently long, and the dimensions of channel 428 sufficient constrained, to retain receiver assembly 420 in engagement with anchor base 410 throughout a full range of motion of receiver assembly 420 and anchor base 410, relative to each other.

While pin 426 is illustrated as being round, other shapes are possible, including elongated shapes. Additionally, pin 426 may fit loosely within both channel 428 and channel 430, being retained by some other means, for example a retainer engageable with pin 426, or a blocking member placed at an outlet of channel 428 or 430. While neither retaining means are illustrated, their design is within the abilities of one skilled in the art.

While pin 426 is illustrated in two parts, one on each side of receiver assembly 420, pin 426 could be formed as a single shaft or elongated pin 426 passing from one side of receiver assembly to another (not shown). In this event, it may be advantageous to tighten anchor fastener 114 prior to insertion of pin 426.

Figure 14:
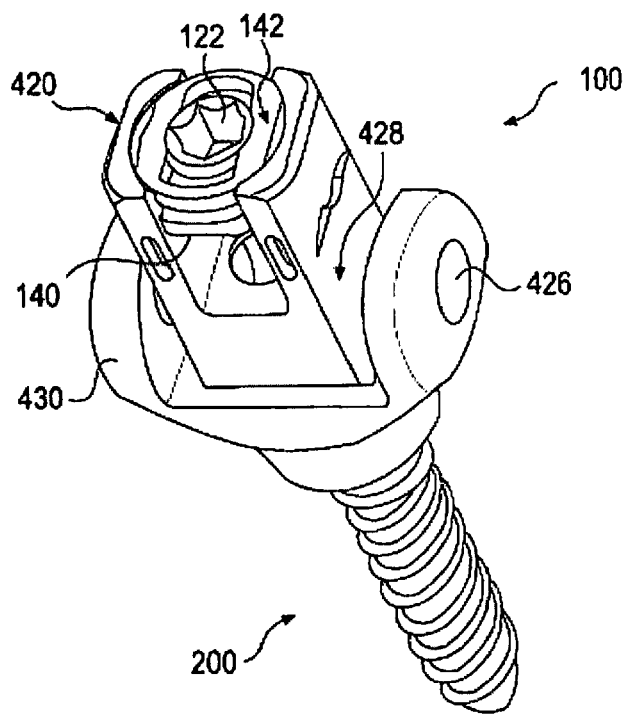
FIG. 14 is a perspective view of a stabilizing receiver in accordance with the invention, enabling conforming shifting in two dimensions.
Figure 15:
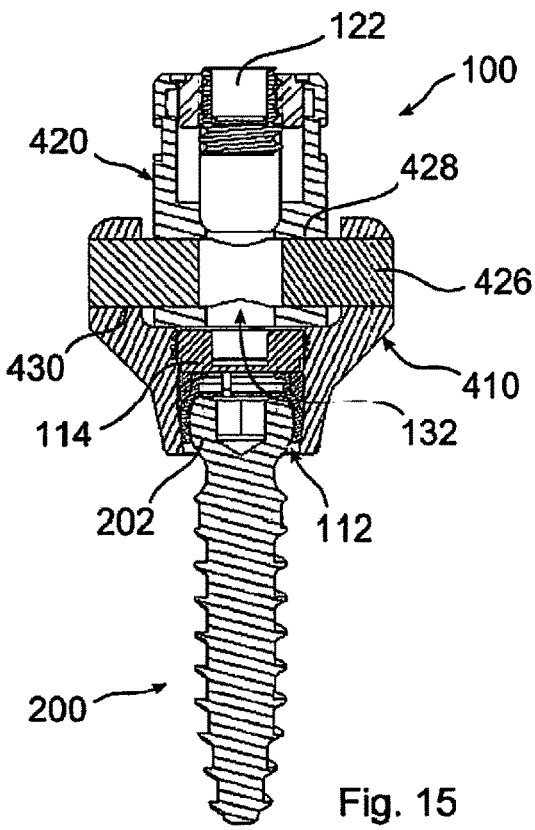
FIG. 15 is a cross sectional illustration of the receiver of FIG. 14, taken along a longitudinal centerline of the receiver.
Figure 16:
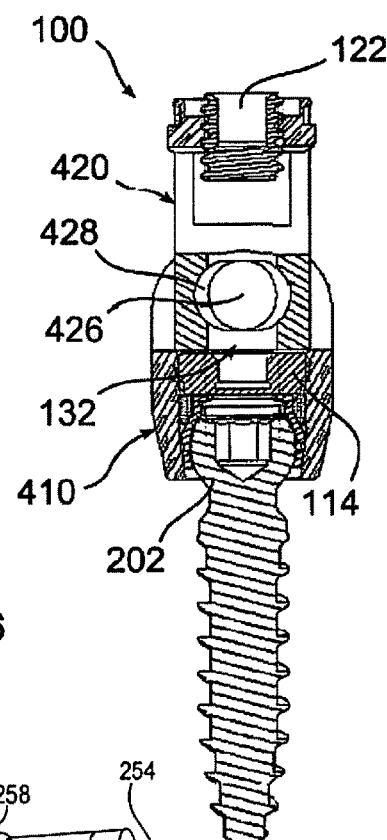
FIG. 16 is a cross sectional illustration of the receiver of FIG. 14, taken along a longitudinal centerline of the receiver, rotated 90 degrees with respect to FIG. 15.

FIG. 13A illustrates the receiver of FIG. 13, rotated about a longitudinal axis 90 degrees, with only an outline of anchor base 410 shown, in order to better view an embodiment of channel 428. FIG. 14 is a perspective view of an embodiment of the form of receiver depicted in FIG. 13.

Figure 17:
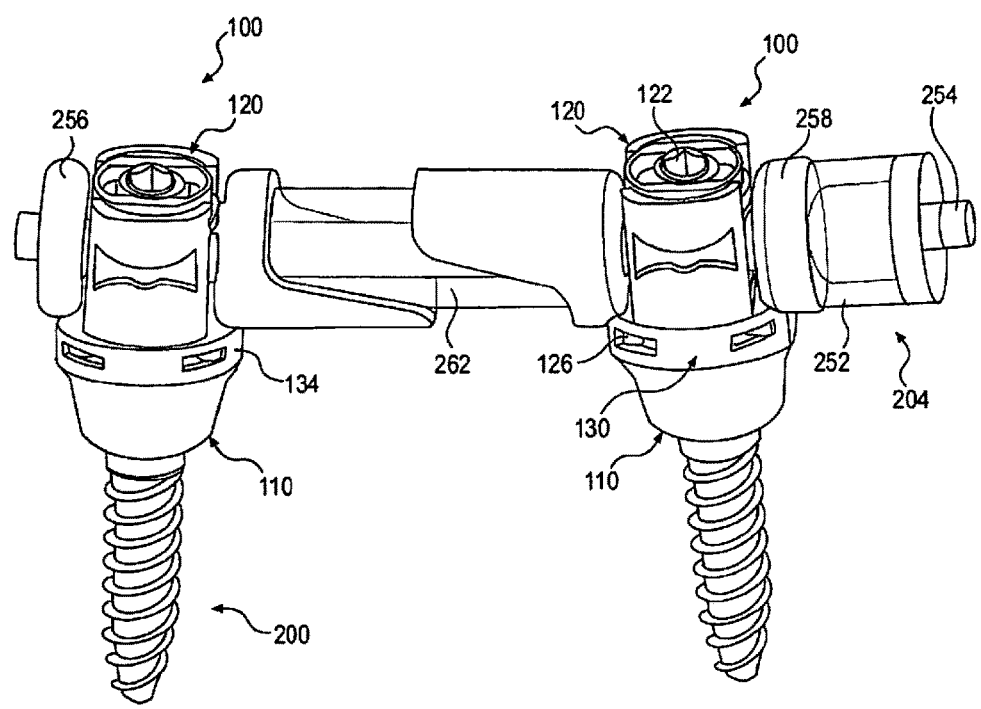
FIG. 17 is a perspective view of two receivers of FIG. 2 connected to a stabilizing means.

FIG. 17 illustrates two receivers 100 mutually connected to a stabilizing means 204, such as that shown and described, for example, in incorporated U.S. Patent application 2009/0299411 to Laskowitz. Stabilizing means 204, in this example, includes spool 258, end plate 256, flexible intermediate portion 263, and cord 254, all having a form and function as described in the aforementioned application, with the following distinctions. Receivers 100, in accordance with the instant invention, are used to connect stabilizing means 200 to the patient. As such, certain movements of joint portions are not fully transmitted to mating joint portions, or to the stabilizing means connecting the joint portions. For example, shifting movements of joint portions directionally aligned with the implanted direction of channels 128, 130, tend to cause relative movement of anchor base 110 and receiver assembly 120, and thus less force is transmitted to adjoining joint portions.

More particularly, and with reference to FIGS. 18-19, flexion of a simplified series of joints is illustrated, in which three bones are provided with receivers 100 in accordance with the invention. The drawings are diagrammatic, and are not to scale, to best illustrate a functionality of the embodiments to be described. Each joint portion 206 has been connected to a receiver 100 by anchor 200, whereby each anchor body 110 moves and rotates with its respective joint portion. It should be understood that while three levels, or jointed portions, are illustrated, any number of receivers and jointed portions may be connected as shown and described herein. Similarly, it should further be understood that a single receiver may be used, wherein a portion of stabilizing means 204 are connected to the body in some other way, for example by a different form of connector, or by suture, staple, screw, glue, or any other method, and another portion of stabilizing means is connected to receiver 100.

Figures 18A, 18B:
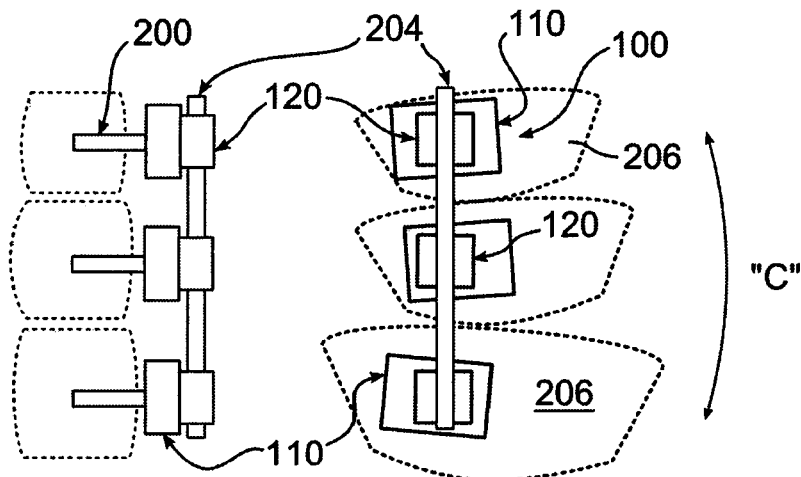
FIGS. 18A-B are schematic illustrations of three receivers corresponding to the receiver of FIG. 13, stabilizing three bones of a patient and using a rigid stabilizing means.

In FIGS. 18A-B, receiver assemblies 120 are of the type illustrated in FIG. 13, and are free to shift laterally and rotate axially, as described herein. In FIGS. 18A-B, stabilizing means 204 is a rod that is substantially inflexible relative to movement of the jointed bones 206. Each receiver assembly 120 is connected to rod 204, as described elsewhere herein, although this connection is not illustrated, for clarity. As the joint segments are flexed in a direction indicated by arrow "C", anchor bases 110 are each rotated, and brought closer to one another. As rod 204 does not bend, a rotating and a shifting force is imparted to an interface between anchor bases 110, and receiver assemblies 120. Consequently receiver assemblies 120 shift and rotate relative to their respective anchor bases 110, as illustrated in FIG. 18B. Viewed from a side, in FIG. 18A, it can be seen that an anterior/posterior flexion/extension is therapeutically inhibited, while a lateral flexion is enabled.

Figures 19A, 19B:
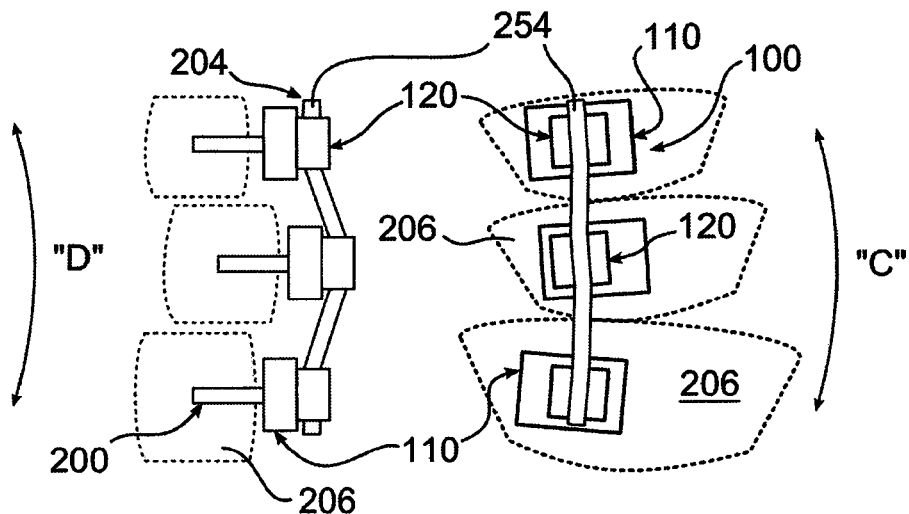
FIGS. 19A-B are schematic illustrations of three receivers corresponding to the receiver of FIG. 2, stabilizing three bones of a patient and using a flexible stabilizing means.

With reference to FIGS. 19A-B, stabilizing means 204 is a flexible cord 254 that readily bends, but is resistant to stretching, as more fully described in the incorporated references. Other stabilizing components which may be used together with cord 254, as described in the incorporated references, are not shown, for clarity. In this illustration, the bones of the joints are engaged in both lateral flexion, indicated by arrow "C", and flexion/extension, indicated by arrow "D". Receivers 100 are representative of the embodiment shown in FIG. 2, which enable a lateral shifting of receiving assembly 120 and anchor base 110. As may be seen in the illustrations, cord 254 bends as it enters and exits receiver assemblies 120; however, a maximum separation of the jointed bones is maintained. Further, it may also be seen that receiver assembly 120 is shifted from a centerline of receiver 100, particularly in the lower two receivers 100 illustrated. This provides additional range of motion for the patient, while maintaining an effective therapeutic stabilization.

Receivers 100 of the invention are useful in a wide variety of clinical situations, including total disc replacements, including situations in which both facets remain, or where one or more facets are removed. In particular, receiver 100 permits lateral or axial rotation, but prevents excess shear forces being exerted upon the spine, which in turn could cause instability and possibly alter the center of rotation of a spinal motion segment. The invention may thus be used in conjunction with other implanted components, including an artificial or grafted disc replacement component. Examples of other implanted components which may be used in conjunction with embodiments disclosed herein may be found in U.S. patent application Ser. Nos. 10/827,642; 10/909,210; 11/246,149; 11/318,438; 11/364,160; 11/36, 390; 12/623,725; 12/729,400; 12/466,680; 12/632,267; and Ser. No. 12/699,648, which are incorporated by reference herein.

Figure 20:
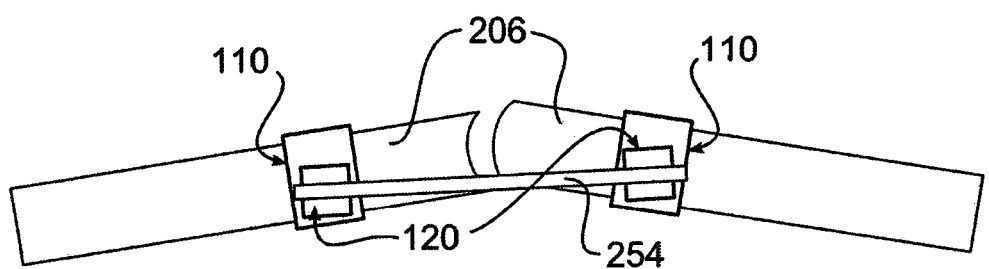
FIG. 20 is a schematic illustration of receivers in accordance with the invention stabilizing elongated bones of a patent.

FIG. 20 illustrates that a receiver 100 of the invention may be used with elongated bones of a body. Accordingly, receivers in accordance with the invention may be used with bones or tissue anywhere in the body, including the toe, foot, ankle, calf, knee, thigh, hip, spine, shoulder, head, jaw, upper arm, elbow, lower arm, wrist, hand, and finger. Receivers 100 of the invention may additionally be used to stabilize rigid tissues, such as bones or cartilage, which have been damaged, for example by disease or trauma. For example, the receivers may be placed on opposite sides of a fracture, permitting therapeutic movement in one plane, but not in another.

In accordance with the invention, prior to installation of receiver 100, it may be advantageous to first assemble wedges 136 onto anchor 200, pass anchor 200 through access bore 132 into bone screw chamber 112, seat receiving assembly 120 onto anchor base 110, and insert tiebar 126 or pins 426, after which the assembly may be sterilized and packaged. Other parts are also sterilized and packaged. The assembly just described may be installed into bone using the methods and tools described in the incorporated references, including the implantation and tightening of anchor 200 and stabilizing means 204. Prior to installing stabilizing means 204, anchor fastener 114 is installed and tightened. Advantageously, the same tool may be used to fasten anchor fastener 114 and stabilizer fastener 122, for example a single hex head driver. The foregoing assembly procedure may be altered, for example components may be assembled prior to implantation, and disassembled at a time of use.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method of spinal stabilization comprising:
   inserting a first receiver assembly into a first bone member;
   inserting a second receiver assembly into a second bone member, wherein at least one of the first and second receiver assemblies includes:
   a base defining a longitudinal axis, the base having an external wall around the longitudinal axis and an internal wall defining an elongate groove;
   a fastener connecting the base to the bone member;
   a receiver disposed on the base and including a first extension and a second extension for receiving an elongate rod therein, the receiver including an elongate projection slidably coupled to the elongate groove for translational movement lateral to the longitudinal axis;
   inserting the elongate rod through the inserted first and second receiver assemblies to fix the first and second assemblies together
   wherein from a front view, the first extension and the second extension form part of a U-shaped channel for receiving the elongate rod therein and the projection is blocked from view by a surface of the base.

2. The method of claim 1, wherein the at least one of the first and second assemblies further includes a second projection connectable to one of the base and the receiver.

3. The method of claim 2, wherein the second projection is operable to limit the translational movement of the receiver relative to the base.

4. The method of claim 2, wherein the second projection is positioned adjacent to an end of the projection.

5. The method of claim 1, wherein the base includes a chamber for receiving the fastener and a clamping element for clamping a head of a bone screw within the chamber.

6. The method of claim 1, wherein the first extension and second extension are configured to receive a set screw.

7. The method of claim 1, wherein the groove extends along at least two sides of the base.

8. The method of claim 1, wherein the projection is a flange extending along at least two sides of the receiver.

9. The method of claim 1, further comprising a retaining tie bar disposed in the groove.

10. The method of claim 1, wherein:
    the at least one of the first and second receiver assemblies further includes:
    a stabilizing fastener adapted to engage a chamber of the receiver through an interlocking channel of the receiver; and
    a set screw threadably received in the stabilizing fastener for securing the rod member.

11. The method of claim 10, further comprising rotating the stabilizing fastener to lock the stabilizing fastener in the interlocking channel of the receiver.

12. A method of spinal stabilization comprising:
    inserting a spinal system into a spine of patient, wherein the spinal system includes:
    a bone screw being polyaxial and including a tapered shaft;
    a base defining a longitudinal axis and including a bone screw chamber for receiving the bone screw therein, the base having an external wall around the longitudinal axis and an internal wall defining an elongate groove;
    a receiver connected to the base, and including a first extension and a second extension, wherein the first extension and the second extension form a channel therethrough, the receiver including an elongate projection slidably coupled to the elongate groove for translational movement lateral to the longitudinal axis;
    a stabilizing member insertable in the channel between the first extension and the second extension, wherein the stabilization member includes a rod member,
    wherein at least one of the receiver and the base includes a limiting surface to limit translational movement of the receiver relative to the base, and
    wherein from a front view, the first extension and the second extension form part of a U-shaped channel for receiving the stabilizing member therein and the projection is not outwardly visible.

13. The method of claim 12, wherein the spinal system further includes a set screw received downwardly through the channel.

14. The method of claim 12, wherein the stabilizing member is rigid or flexible.

15. The method of claim 12, further comprising a tie bar disposed in the groove, wherein the receiver slides relative to the base along the tie bar.

16. The method of claim 12, wherein from a bottom to top direction, the receiver has a bottommost width that is greater than or equal to an uppermost width.

17. The method of claim 12, wherein a gap between the projection and the groove enables relative movement between the receiver and the base in the lateral direction.

18. The method of claim 12, further comprising a limiting member for limiting a range of lateral movement between the receiver and the base, wherein the limiting member is positioned adjacent to an end of the projection.

19. The method of claim 12, wherein:
the spinal system further includes:
a stabilizing fastener adapted to engage the chamber above the rod member through an interlocking channel in the first and second extensions; and
a set screw threadably received in the stabilizing fastener for securing the rod member.

* * * * *